United States Patent [19]

Andress, Jr. et al.

[11] 4,410,434

[45] Oct. 18, 1983

[54] METAL SALTS OF PHOSPHOSULFURIZED POLYHYDROXYESTERS AND LUBRICANTS CONTAINING SAME

[75] Inventors: Harry J. Andress, Jr., Wenonah; Andrew G. Horodysky, Cherry Hill; Joan M. Kaminski, Clementon, all of N.J.

[73] Assignee: Mobil Oil Corporation, New York, N.Y.

[21] Appl. No.: 274,614

[22] Filed: Jun. 17, 1981

Related U.S. Application Data

[63] Continuation-in-part of Ser. No. 113,149, Jan. 18, 1980, abandoned.

[51] Int. Cl.$^3$ .............................................. C10M 1/48
[52] U.S. Cl. ............................. 252/32.7 R; 260/125; 260/429 R; 260/429.9
[58] Field of Search ...................... 252/32.7 R, 32.7 E; 260/429 R, 429.9, 125

[56] References Cited

U.S. PATENT DOCUMENTS

| | | | |
|---|---|---|---|
| 2,422,206 | 6/1947 | Musselman | 252/32.7 E X |
| 2,422,630 | 6/1947 | Musselman et al. | 252/32.7 E X |
| 3,288,819 | 11/1966 | Tichelaar et al. | 252/32.7 E X |
| 3,682,819 | 8/1972 | Morris et al. | 252/32.7 E |

*Primary Examiner*—Andrew Metz
*Attorney, Agent, or Firm*—Alexander J. McKillop; Michael G. Gilman; Howard M. Flournoy

[57] ABSTRACT

The invention herein is concerned with novel compositions of matter made by reacting phosphorus pentasulfide with a polyhydroxyester and then followed by reaction with a salt-forming metal-containing compound and lubricant compositions containing same.

18 Claims, No Drawings

METAL SALTS OF PHOSPHOSULFURIZED POLYHYDROXYESTERS AND LUBRICANTS CONTAINING SAME

CROSS REFERENCE TO RELATED APPLICATIONS

This application is a continuation-in-part of U.S. application Ser. No. 113,149, filed Jan. 18, 1980, for "METAL SALTS OF PHOSPHOSULFURIZED POLYHYDROXYESTERS AND LUBRICANTS CONTAINING SAME" and now abandoned.

BACKGROUND OF THE INVENTION

1. Field of the Invention

The invention is concerned with a novel group of compounds and their use as friction reducing and antiwear additives in lubricants, i.e. lubricant compositions containing same.

2. Discussion of the Prior Art

It is known that sliding or rubbing metal or other solid surfaces are subject to wear under conditions of extreme pressure. Wearing is particularly acute in modern engines in which high temperatures and contact pressures are prevalent. Under such conditions, severe erosion of metal surfaces can take place even with present generation lubricants unless a load carrying or antiwear additive is present therein.

Friction is also a problem any time two surfaces are in sliding or rubbing contact. It is of especial significance in an internal combustion engine, because loss of a substantial amount of the theoretical mileage possible from a gallon of fuel is traceable directly to friction.

Phosphorus compounds are known to be useful as additives to lubricants to improve some property thereof, e.g. the antiwear property. Further, lubricants containing metal salts of phosphorus acids are also known. However, no prior art is known disclosing or suggesting the reaction product of the present invention.

SUMMARY OF THE INVENTION

In accordance with the invention, there is provided a compound prepared by (1) reacting phosphorus polysulfide, particularly phosphorus pentasulfide with an ester or mixture of esters of the formula

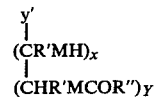

where R" is hydrocarbyl containing 2 to 30 carbon atoms, R' is hydrogen or a lower alkyl containing 1 to 6 carbon atoms, M is oxygen or sulfur, x is 1 to 5, y is 1 to 3 and y' is hydrogen or $(CHR'MCOR'')_y$ and (2) reacting the product of (1) with a salt-forming metal-containing compound.

The invention also provides a lubricant composition comprising lubricant and the said compound.

The above formula includes a variety of esters. Among those that may be mentioned have the formulae

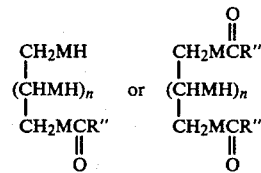

wherein M and R" are as defined above and n is 1 to 2.

The invention also provides a lubricant composition comprising the reaction product.

DESCRIPTION OF SPECIFIC EMBODIMENTS

The novel compounds of this invention are made by (1) reacting, for example, phosphorus pentasulfide ($P_2S_5$) with an ester having the formula set forth hereinabove and (2) reacting the resulting product with a metal-containing compound. The product of the first reaction is a complex one and its structure is not known, although it may contain one or more of the following structures, illustrated with a glycerol monocarboxylate:

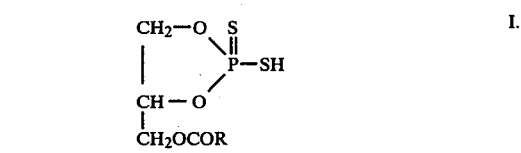

I.

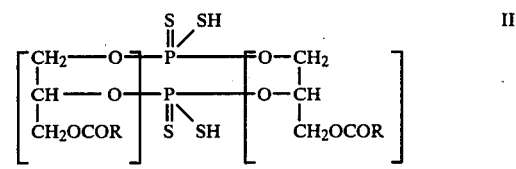

II.

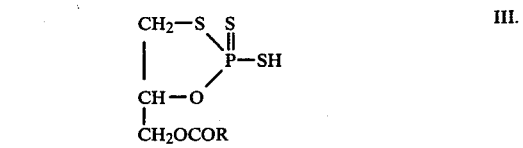

III.

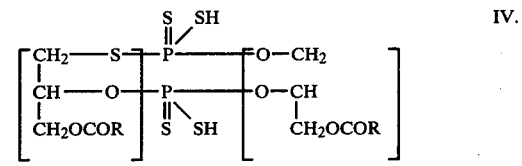

IV.

These structures would require 2 moles of the glycol per mole of $P_2S_5$.

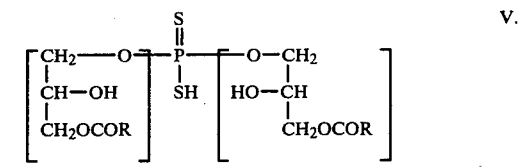

V.

or

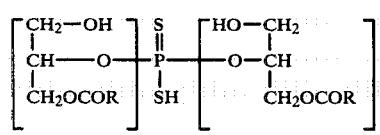

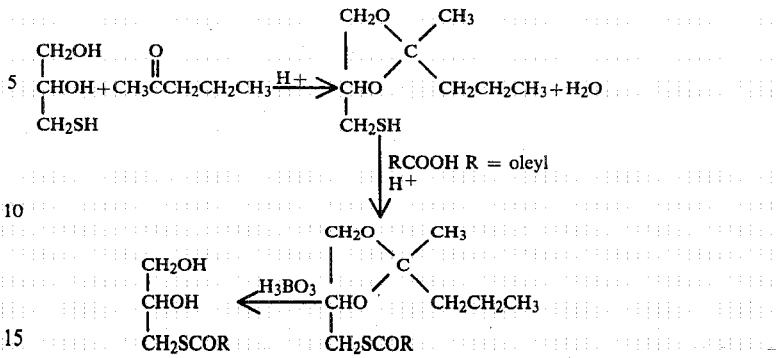

Structures V and VI would require 4 moles of glycol per mole of $P_2S_5$. However, the amount of reactants in reaction (1) is not limited to the stated ratios. It is contemplated that in that reaction, from about 2 moles to about 12 moles of ester, preferably from about 2 moles to about 4 moles, can be used per mole of $P_2S_5$. The temperature of this reaction can be within the range of from about 60° C. to about 140° C., preferably from about 90° C. to about 110° C.

Although the reaction is usually conducted without a solvent, one can be used if desired. Any unreactive, easily removable solvent is suitable, and these include benzene, toluene, xylene and 1-4 dioxane.

Reaction (2) can be carried out at from about 50° C. to about 125° C., preferably from about 70° C. to about 100° C. Stoichiometric amounts of the metal-containing compound may be used, or, if desired, an excess of up to 100% of theory, preferably from about 5% to about 10% by weight can be used, with removal of the unreacted excess. By "stoichiometric amounts" is meant sufficient amount of the metal-containing compound to supply the metal required to react with all the acid groups present in the complex product.

The metal ion or metal ion-containing radical of the compound is selected such that the metal is manganese or is from Groups IIA, IIB, VIB or VIII of the Periodic Chart. Mixtures of these metals are also contemplated. Illustrative metals from the respective groups are calcium and strontium; zinc and cadmium; chromium and molybdenum; and nickel. These can be contained in salts having, for example, the carbonate, the halide (e.g. the chloride or bromide) or the nitrate ion. The metal may also be in the form of its oxide or hydroxide or it can be a portion of an acid, as, for example, molybdic acid. Generally preferred are the oxide, the carbonate and the halide.

While atmospheric pressure is gradually preferred in reaction (2), reaction (1) or (2) can be advantageously run at from about 0.5 to about 2 atmospheres. Furthermore, where conditions warrant it, a solvent may be used in reaction (2). Useful solvents for the reaction include the alcohols, e.g. isopropanol, or benzene or toluene containing from about 5% to about 15% of the alcohol.

Water catalyzes the reaction, and reaction progress is enhanced if a catalytic amount thereof is added to the reaction mixture for reaction (2).

The times of reactions are not critical. Thus, any phase of the process can be carried out in from 1 to 8 hours.

Most of the useful esters are commercially available as mixtures of the mono- and diesters. While these may be used where the monoester is the predominant form, the pure monoester can be prepared by known methods. For example, the preferred monothioglycerol monooleate can be prepared pure as follows:

Of particular significance, in accordance with the present invention, is the ability to improve the friction properties of oleaginous materials such as lubricating media which may comprise either a mineral oil or a synthetic oil, or a grease therefrom. In general, mineral oils, either paraffinic, naphthenic or mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800.

In instances where synthetic oils are desired in preference to mineral oils, or in combination therewith, various compounds of this type may be successfully utilized. Typical synthetic vehicles include polyisobutylene, polybutenes, hydrogenated polyolefins, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis (p-phenoxy phenol) ether, phenoxy phenylethers.

It is to be understood, however, that the compositions contemplated herein can also contain other materials. For example, corrosion inhibitors, extreme pressure agents, viscosity index improvers, co-antioxidants, anti-wear agents and the like can be used. These materials do not direct from the value of the compositions of this invention, but rather they serve to impart their customary properties to the particular compositions in which they are incorporated.

In general, the preformed adducts of the present invention may be employed in any amount which is effective for imparting the desired degree of friction reduction or antiwear activity. In many applications, however, the adduct is effectively employed in amounts from about 0.1% to about 10% by weight, and preferably from about 0.5 to about 5% of the total weight of the composition.

The following Examples will present illustrations of the invention. They are illustrative only, and are not meant to limit the invention.

EXAMPLE 1

Synthesis of Monothioglycerol Monooleate

A mixture of 1-thioglycerol (70.5 g.), 2-pentanone (277 g.), and p-toluene sulfonic acid (2 g.) were refluxed until the expected 20 cc. of water formed and was azeotroped off. Oleic acid (163 g.) was added to the reaction solution which was then refluxed until the expected 10 cc. of $H_2O$ azeotroped off. Toluene (800 cc.) was added to the cooled reaction solution, which was then shaken with sodium acetate (6 g.), washed with $H_2O$ (4×400 cc.), and dried over sodium sulfate. The toluene solution was filtered and had solvents removed via high speed rotary evaporation under reduced pressure. The resulting yellow fluid (190 g.) was refluxed in monomethyl ethylene glycol (520 cc.) with boric acid (103 g.) at 100° C. for 2 hours. Ether was added (875 cc.) and the entire solution was transferred to a separatory funnel, washed with water (4×750 cc.), washed with 13% sodium bicarbonate solution (2×100 cc.) and washed with water (2×100 cc). The ether solution was shaken with sodium acetate (14 g.) and 100 cc. of water and then washed with a saturated sodium chloride solution (3×150 cc.). The ether solution was dried over magnesium sulfate, stripped free of solvent, and filtered through diatomaceous earth to yield a clear bright yellow oil. Gel permeation chromatography showed that the product was acid free (oleic) and contained approximately 80% monothioglycerol monooleate and 20% monothioglycerol dioleate.

EXAMPLE 2

Synthesis of Partially Phosphosulfurized Monothioglycerol Monooleate

Monothioglycerol monooleate (140 g.) prepared as described in Example 1, was heated at 90°–110° C. with phosphorus pentasulfide, $P_2S_5$ (21 g.), which was added batchwise.

After 3–4 hours, hydrogen sulfide evolution had ceased and the resulting slightly viscous, orange fluid was filtered through diatomaceous earth to remove small amounts of unreacted $P_2S_5$.

EXAMPLE 3

Synthesis of Zinc Salt of Partially Phosphosulfurized Monothioglycerol

A mixture of partially phosphosulfurized monothioglycerol monooleate (59 g.), prepared as described in Example 2, zinc oxide (15 g.), and isopropanol (150 cc.) with a few drops of water was refluxed for 5 hours. The solvent was removed by high speed rotary evaporation under reduced pressure, and the product was filtered through diatomaceous earth yielding a fluid, orange liquid.

EXAMPLE 4

Synthesis of Molybdenum Salt of Partially Phosphosulfurized Monothioglycerol Monooleate Sodium molybdate (45 g.) in 150 cc. of $H_2O$, acidified to a pH of 4–5 with concentrated sulfuric acid, was added dropwise to partially phosphosulfurized monothioglycerol monooleate (52 g.), prepared as described in Example 2, in isopropanol (130 cc.). The mixture was refluxed for 2 hours, and the solvents were removed by high speed rotary evaporation under reduced pressure. Inorganic salts were filtered from the reaction product yielding a greenish black oil.

EXAMPLE 5

Synthesis of Partially Phosphosulfurized Glycerol Monooleate

Glycerol monooleate (511 g.) obtained commercially as a 60:40 mono-dioleate mixture, was heated to 100°–110° C. with phosphorus pentasulfide, $P_2S_5$, (61 g.), which was added batchwise. After 3 hours, hydrogen sulfide evolution had stopped and the reaction mixture was filtered through diatomaceous earth to remove a small amount of unreacted $P_2S_5$. The product was a slightly viscous orange liquid.

EXAMPLE 6

Synthesis of Phosphosulfurized Glycerol Monooleate

Glycerol monoleate (1508 g.), obtained commercially as a 60:40 mono/dioleate mixture, was heated to 90°–100° C. with phosphorus pentasulfide, $P_2S_5$, (371 g.), which was added batchwise. After 4 hours, hydrogen sulfide evolution ceased and the reaction mixture was filtered to remove small amounts of unreacted $P_2S_5$. The product was a slightly viscous orange liquid.

EXAMPLE 7

Synthesis of Zinc Salt of Partially Phosphosulfurized Glycerol Monooleate

A mixture of partially phosphosulfurized glycerol monooleate (215 g.), prepared as described in Example 5, zinc oxide (24 g.), and isopropanol (300 cc.) with a few drops of water was refluxed for 2 to 4 hours. The solvent was removed by high speed rotary evaporated under reduced pressure and the product was filtered through diatomaceous earth yielding a fluid, orange liquid.

EXAMPLE 8

Synthesis of Zinc Salt of Phosphosulfurized Glycerol Monooleate

A mixture of phosphosulfurized glycerol monooleate (50 g.) prepared as described in Example 6, zinc oxide (12.5 g.), and isopropanol (200 cc.) with a few drops of water was refluxed for 4 hours. The mixture was filtered through diatomaceous earth and the solvent was removed by high speed rotary evaporation under reduced pressure, yielding a viscous yellow liquid.

EXAMPLE 9

Synthesis of Molybdenum Salt of Partially Phosphosulfurized Glycerol Monooleate Sodium molybdate (78 g.) in 100 cc. $H_2O$, acidified to a pH of 4–5 with concentrated hydrochloric acid, was partially added to phosphosulfurized glycerol monooleate (223 g.), prepared as described in Example 5, in isopropanol (300 cc.). The mixture was refluxed for 2 hours, and the solvents were removed by high speed rotary evaporation under reduced pressure. Inorganic salts precipitated from the reaction residue upon standing. Toluene was added, and the toluene soluble portion was filtered and stripped of solvent yielding a dark bluish-green oil.

EVALUATION OF THE COMPOUNDS

The compounds were evaluated in a low velocity friction apparatus (LVFA) in a fully formulated 5W-20 synthetic oil containing 20% by weight of an additive package including antioxidant, dispersant and detergent, as well as a friction reducing compound such as a zinc dithiophosphate. The base oil had the following characteristics

| Kinematic Viscosity | @ 100° C. | 6.8 cs |
|---|---|---|
| | @ 40° C. | 36.9 cs |
| Viscosity Index | | 143 |

The friction reducing compounds were present within the range of 1–5% of the total weight of oil.

Description

The Low Velocity Friction Apparatus (LVFA) is used to measure the coefficient of friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.²). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam-motor arrangement.

Procedure

The rubbing surfaces and 12–13 ml. of test lubricants are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 min. at 250° F., 240 psi, and 40 fpm sliding speed. Afterward, measurements of $U_k$ vs. speed were taken at 240, 300, 400, and 500 psi. Freshly polished steel specimens are used for each run. The surface of the steel is parallel ground to 4 to 8 micro-inches. The results in Table 1 refer to percent reduction in friction compared to the unmodified oil. That is, the formulation mentioned above was tested without the compound of this invention and this became the basis for comparison. The results were obtained at 250° F. and 500 psi.

The compounds were also evaluated as copper strip corrosion inhibitors in accordance with ASTM D-130.

TABLE 1

| | | Change in Coefficient of Friction on Low Velocity Friction Apparatus | | |
|---|---|---|---|---|
| | Conc. of Additive % wt. in base oil | Reduction in Coef. of fric. at Sliding Speeds of | | Cu Corrosion[b] 6 hr., 210° F. |
| Composition | | 5 ft./min. | 30 ft./min. | |
| Base Oil | 0 | 0[a] | 0[a] | 1A |
| Base Oil + Example 3 | 4 | 32 | 23 | 1A |
| | 2 | 13 | 9 | |
| Modified base oil similar to above but containing no zinc dithiophosphate other than the product of Example 3 | 5 | 45 | 34 | 1B |
| Base Oil + Example 4 | 4 | 18 | 21 | |
| Modified base oil + Example 7 similar to above, but containing no zinc dithiophosphate other than the product of Example 7 | 5 | 36 | 23 | 1A |
| Base Oil + Example 8 | 4 | 45 | 35 | 1A |
| | 2 | 32 | 24 | |
| | 1 | 11 | 10 | |
| Base Oil + Example 9 | 4 | 27 | 23 | 1A |

[a]Value for base fluid assigned at zero point.
[b]ASTM D-130.

We claim:
1. A compound prepared by
   (1) reacting at a temperature of from about 60° C. to 140° C., about 1 mole of a phosphorus polysulfide with from about 2 to about 12 moles of an ester or mixtures of esters of the formula

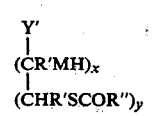

where R″ is hydrocarbyl containing 2 to 30 carbon atoms, R′ is hydrogen or a lower alkyl containing 1 to 6 carbon atoms, M is oxygen or sulfur, x is 1 to 5, y is 1 to 3 and Y′ is hydrogen or (CHR′SCOR″)$_y$ and (2) reacting the product of (1) at a temperature of from about 50° C. to about 125° C. with from about a stoichiometric amount to a 100% excess of a salt-forming metal-containing compound wherein the metal in said metal-containing compound is selected from the group consisting of manganese, metals from Groups IIA, IIB, VIB or VIII of the Periodic Chart and mixtures thereof.

2. The compound of claim 1 wherein the polysulfide is pentasulfide.

3. The compound of claim 1 wherein said metal is zinc.

4. The compound of claim 1 wherein said metal is molybdenum.

5. The comound of claim 1 wherein the ester has the formula

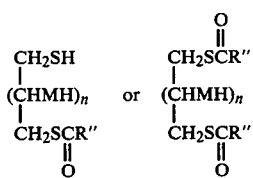

wherein M is sulfur, R" is a hydrocarbyl containing 2 to 30 carbon atoms and n is 1 to 2.

6. The compound of claim 1 wherein the ester is

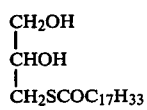

the polysulfide is pentasulfide and the metal is zinc.

7. The compound of claim 1 wherein the ester is

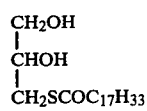

the polysulfide is pentasulfide and the metal is molybdenum.

8. A composition comprising a major proportion of an oil of lubricating viscosity or grease prepared therefrom and a minor friction reducing amount of a compound prepared by (1) reacting at a temperature of from about 60° C. to about 140° C., one mole of a phosphorus polysulfide with from about 2 to about 12 moles of an ester or mixtures of esters of the formula

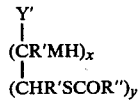

where R" is hydrocarbyl containing 2 to 30 carbon atoms, R' is hydrogen or a lower alkyl containing 1 to 6 carbon atoms, M is oxygen or sulfur, x is 1 to 5, y is 1 to 3 and Y' is hydrogen or (CHR'SCOR")$_y$ and (2) reacting the product of (1) at a temperature of from about 50° C. to about 125° C. with from about stoichiometric amounts to a 100% excess of a salt-forming metal-containing compound wherein the metal in said metal-containing compound is selected from the group consisting of manganese, metals from Groups IIA, IIB, VIB or VIII of the Periodic Chart and mixtures thereof.

9. The composition of claim 8 wherein the lubricant is a lubricating oil.

10. The composition of claim 8 wherein the lubricant is a grease.

11. The composition of claim 9 wherein the lubricating oil is a synthetic lubricating oil.

12. The composition of claim 8 wherein the polysulfide is pentasulfide.

13. The composition of claim 8 wherein said metal is zinc.

14. The composition of claim 8 wherein said metal is molybdenum.

15. The composition of claim 8 wherein said ester has the formula

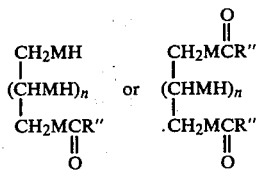

wherein M is sulfur, R" is a hydrocarbyl containing 2 to 30 carbon atoms and n is 1 to 2.

16. The composition of claim 8 wherein the ester is

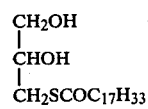

the polysulfide is pentasulfide and the metal is zinc.

17. The compound of claim 1 wherein said polysulfide and said ester or mixtures of esters in molar amounts of from about 2 to 4 moles of said ester or esters to one mole of said sulfide are reacted at a temperature of from about 90° C. to about 110° C., and the reaction product thereof and an excess of about 5 to about 10 wt% of the stoichiometric amount of said salt forming metal-containing compound are reacted at a temperature of from about 70° C. to about 100° C.

18. The composition of claim 8 wherein said polysulfide and said ester or mixtures of esters in molar amounts of from about 2 to 4 moles of said ester or esters to one mole of said sulfide are reacted at a temperature of from about 90° C. to about 110° C., and the reaction product thereof and an excess of about 5 to about 10 wt% of the stoichiometric amount of said salt forming metal-containing compound are reacted at a temperature of from about 70° C. to about 100° C.

* * * * *